United States Patent [19]

Greenway, III et al.

[11] Patent Number: 4,588,724

[45] Date of Patent: May 13, 1986

[54] TREATMENT FOR SELECTIVE REDUCTION OF REGIONAL FAT DEPOSITS

[76] Inventors: Frank L. Greenway, III, 4560 Admiralty Way, Suite 301, Marina Del Rey, Calif. 90291; George A. Bray, 234 S. Figueroa, #1035, Los Angeles, Calif. 90012

[21] Appl. No.: 690,651

[22] Filed: Jan. 11, 1985

Related U.S. Application Data

[62] Division of Ser. No. 448,836, Dec. 10, 1982, Pat. No. 4,525,359.

[51] Int. Cl.$^4$ .................... A61K 31/44; A61K 31/50; A61K 31/445; A61K 31/495
[52] U.S. Cl. .................... 514/250; 514/280; 514/321; 514/400; 514/909
[58] Field of Search ............... 514/250, 280, 321, 400, 514/909

[56] References Cited

PUBLICATIONS

Chem. Abst. 92: 28565m (1980)–Sandoz A–G.
Chem. Abst. 96: 91641f (1982)–Navarro et al.
Chem. Abst. 101: 168203a (1984)–Callahan et al.
Chem. Abst. 101: 144000(b) (1984)–Dulloo et al.

*Primary Examiner*—Douglas W. Robinson
*Attorney, Agent, or Firm*—Fulwider Patton Rieber Lee & Utecht

[57] ABSTRACT

A treatment for accelerating regional weight reduction in humans, wherein an active ingredient encouraging elimination of fatty deposits, preferably a beta adrenergic stimulator or an alpha-2 adrenergic inhibitor, is selectively delivered to a regional fat deposit prior to commencing or during a general weight control program, whereby body weight is preferentially reduced in the selected area. The beta adrenergic stimulator, preferably isoproterenol or forskolin, or the alpha-2 adrenergic inhibitor, preferably yohimbine, or combinations thereof may be delivered by any means accomplishing specific delivery to the selected area, including injection, implantation, and topical application to the skin as in an ointment or creme.

14 Claims, No Drawings

TREATMENT FOR SELECTIVE REDUCTION OF REGIONAL FAT DEPOSITS

This is a division of application Ser. No. 448,836, filed Dec. 10, 1982, now U.S. Pat. No. 4,525,359.

BACKGROUND OF THE INVENTION

This invention relates to control of weight loss in humans, and more particularly, to a process wherein weight loss is achieved from selected portions of the body by reduction of regional fat deposits.

When an overweight person reduces body weight through a weight control program, it is often observed that the excess body fat is removed more rapidly from some parts of the body than from other parts. For example, weight loss tends to be more rapid from the abdomen than from the thighs. For a person who loses only a relatively small amount of weight, such differential weight loss during the reduction program is not noticeable. However, overweight persons who must lose larger amounts of weight may be distressed by the failure to achieve normal bodily proportions during the weight control program. Most of the weight loss may come from the abdomen and chest, while the thighs remain excessively overweight. This result is undesirable aesthetically and psychologically, in that the body neither attains proper proportions nor is perceived to approach proper proportions. Additionally, the fatty deposits of the thighs which remain may have a rumpled or "peau-de-orange" appearance, popularly termed "cellulite," which is unattractive and may be particularly distressing. Thus, there exists a significant problem arising in weight control programs as a result of the differential reduction in body fat deposits.

Two approaches have generally been taken to alleviate the problem created by the differential weight loss in weight control programs. In one, the weight loss program is carried to extremes so that the person loses a greater amount of weight than is medically desirable, and eventually weight is lost from all portions of the body. Such excessive weight loss may result in poor health, and still not obtain a desirable physical appearance. In a second commonly used method, the person undergoing weight loss seeks to selectively eliminate remaining fat desposits through an exercise or physical motion program. For example, the thighs may be massaged or vibrated in an attempt to eliminate the fatty deposits thereon. However, such physical weight loss programs are not feasible for all persons and are of questionable effectiveness.

Accordingly, there has been a continuing need for a reliable, effective treatment for accomplishing the selective reduction of regional body fat deposits during a weight control program by accelerating weight loss in areas such as the thighs which normally reduce less rapidly than the abdomen. The present invention fulfills this need, and further provides related advantages.

SUMMARY OF THE INVENTION

The present invention provides a treatment method for achieving a selective loss in body weight during a weight control program, by the selective reduction of regional body fat deposits. Thus, the reduction of those fatty deposits located in areas which normally reduce more slowly may be accelerated. With this invention, a person undergoing a weight control program may achieve a desirable balanced rate of weight loss.

In accordance with the invention, an active ingredient encouraging reduction of fat cells is selectively delivered to a portion of the body where weight reduction is desired, so that accelerated reduction of the regional body fat deposit occurs during a general weight control program, thereby achieving a balanced weight reduction. Preferred active ingredients found useful in accomplishing accelerated reduction of regional body fat deposits include beta adrenergic stimulators, alpha-2 adrenergic inhibitors, and combinations thereof, most preferably the beta adrenergic stimulator isoproterenol. The active ingredient may be delivered to the regional fatty deposit by any means which allows specific delivery, rather than nonspecific delivery, including but not limited to injection, implantation and topical application to the skin in an ointment or creme, for example.

It will be appreciated from the foregoing that the present invention represents a significant advance in control of overweight conditions. With this invention, enhanced reduction of those regional body fat deposits which normally are reduced more slowly during a weight control program is achieved. As a result, the person undergoing a weight control program more rapidly achieves a normal body appearance in a medically acceptable manner.

Other features and advantages of the present invention will become apparent from the following more detailed description of the preferred embodiment, which describes, by way of example, the principles of the invention.

DETAILED DESCRIPTION OF THE PREFERRED EMBODIMENT

The present invention is embodied in a treatment used in conjunction with a general weight loss program, whereby a reduction in regional body fat desposits is selectively accelerated during a general weight control program. In a general weight control program, as that term is used herein, a person seeks to achieve a loss of body weight, normally by a combination of a calorie-restricted diet and exercise. In successful weight control programs, it is often noticed that weight loss occurs more rapidly from certain parts of the body than from other parts, and specifically weight loss tends to be more rapid from the abdomen than from the thighs, at least in part because the fatty deposits in the thighs exhibit a greater resistance to reduction than do the fatty deposits in the abdomen.

In accordance with the invention, an active ingredient encouraging reduction of fatty tissue is selectively delivered to a portion of the body having a regional body fat deposit, so that a selective acceleration in reduction of the regional body fat deposit is achieved during the general weight control program. Preferred active ingredients in accomplishing selective reduction of regional body fat deposits include beta adrenergic stimulators and alpha-2 adrenergic inhibitors, or combinations thereof, most preferably the beat adrenergic stimulator isoproterenol. The active ingredient may be delivered to the fatty deposit by any specific means which allows selective localized delivery, rather than a nonspecific delivery, including but not limited to injection, implantation and topical application to the skin in an ointment or creme.

The fat deposits on an overweight person are observed to be concentrated in particular parts of the body rather than uniformly throughout the body. Concentrated local fat deposits, termed herein regional fat deposits, are typically found in the abdomen and thighs of an overweight person. During a general weight control program, as may be conducted with or without a doctor's care, it is observed that weight is not lost at uniform rates from all of the regional fat deposits. Instead, weight is ordinarily lost more rapidly from the abdomen than from the thighs and hips, so that the thighs and hips may remain disproportionately large even as the abdomen approaches a normal condition.

The medical explanation for the differential weight loss phenomenon is not fully settled. While applicant does not wish to be bound by this possible explanation, it is believed that such differential weight loss results from variations in the rates of lipogenesis and lipolysis within each body location during the weight control program. Lipolysis is apparently mediated in part by the nervous system through action on the beta adrenergic and alpha-2 adrenergic receptors in the fat cells. Previous in vitro studies of adipose tissue excised from persons before and during weight control programs have shown that thigh and abdominal tissue respond differently to drugs known to work through beta and alpha-2 adrenergic receptors. For example, it has been shown in vitro that the lipolytic effect of catecholamines is greater in abdominal fat than in thigh fat, and conversely the antilipolytic effect of insulin is less marked in abdominal fat than in thigh fat. Such studies, while of interest in understanding the problem, provide no suggestion for an in vivo treatment to overcome this condition.

The in vivo neurological control of lipolysis in the fat cell is organized such that activity of the beta adrenergic receptor stimulates lipolysis, while activity of the alpha-2 adrenergic receptor inhibits lipolysis. An agent which activates the beta adrenergic receptor encourages lipolysis, or reduction in size, of the fat cell, while an agent which activates the alpha-2 adrenergic receptor discourges lipolysis of the fat cell. Conversely, in respect to the blocking of lipolysis, an agent which inhibits the alpha-2 adrenergic receptor should encourage lipolysis of the fat cell by reducing blocking effects. Therefore, a beta adrenergic stimulator or an alpha-2 adrenergic inhibitor, or combinations thereof, encourages lipolysis of a fat cell. Additionally, an alpha-2 adrenergic inhibitor may allow lipolysis even in the presence of a drug which stimulates both the beta and alpha-2 adrenergic receptors.

To counteract the greater responsiveness of the fat cells in the abdomen to the lipolytic effects of beta adrenergic stimulation. Applicants have found that in vivo selective delivery and application of active ingredients to regional fat deposits can reduce those deposits preferentially during a weight control program. Specifically, local delivery of a beta adrenergic stimulator encourages lipolysis of fat cells which normally undergo lipolysis only slowly. Local delivery of an increased concentration of an alpha-2 adrenergic inhibitor has a similar effect, for the reason that inhibition of lipolysis is blocked. Examples of known beta adrenergic stimulators include, but are not limited to, theophylline, isoproterenol, forskolin and epinephrine. Examples of known alpha-2 adrenergic inhibitors include, but are not limited to, yohimbine, rauwolscine, piperoxane, phentholamine and dihydroergotamine.

Successful selective reduction of fat cell deposits requires that the beta adrenergic stimulator, the alpha-2 adrenergic inhibitor, or combinations thereof, be specifically delivered to the fatty deposit for which lipolysis is sought. It is believed that a nonspecific delivery throughout the body would result in stimulation of lipolysis in all parts of the body, so that abdominal weight loss would exceed weight loss of the thighs, for example. (The systemic effects of general infusions are discussed in Goodman and Gilman's "The Pharmacological Basis of Theraputics", 6th ed., editors Alfred Goodman Gilman, Lewis S. Goodman and Alfred Gilman, McMillen Publishing Co., 1980 at pages 149-154.)

Specific delivery of the active ingredient which encourages lipolysis of the fat cells may be accomplished by any means whereby a higher concentration is achieved in a specific region of the body. Examples of acceptable delivery systems include injections with a needle and syringe, injections with an air gun, surgical implantation below the surface of the skin, and topical application to the surface of the skin over the regional fat deposit, such as by ointments and creams. After delivery, diffusion of the active ingredient throughout the regional fat deposit may be aided by heating or massaging of the deposit, or similar procedures.

While it is possible for the active ingredient to be administered as a raw chemical, it is preferably to present it as a pharmaceutical formulation preparation. Such a formulation, within the scope of the present invention, can comprise a chemical which encourages lipolysis of the fat cell such as a beta adrenergic stimulator or an alpha-2 adrenergic inhibitor, as above described, together with one or more acceptable carriers therefor and optionally other therapeutic ingredients. The carrier(s) must be "acceptable" in the sense of being compatible with other ingredients of the formulation and not deleterious to the recipient thereof. The formulations should be suitable for local delivery as specified above. Thus, it is understood that the treatment described herein may include the step of bringing into association the active ingredient with a liquid carrier, and then locally delivering the formulation as specified above. Formulations suitable for administration conveniently comprise sterile aqueous solutions of the active chemical, which may be conveniently prepared by mixing the active chemical with water, and after rendering said solution sterile it may be presented in sealed containers.

As described in the example presented below, one effective delivery system for the active ingredient is a sterile saline solution. Such a solution may be delivered to a selected regional fat deposit by one or more injections of such a solution directly into the deposit. Another delivery system would be the preparation of an ointment or cream containing an active ingredient therein. For example, a beta adrenergic stimulator such as forskolin and an alpha-2 adrenergic inhibitor such as yohimbine may be mixed together in any of a number of suitable ointment bases know to pharmacologists, such as Aquaphor, and applied topically to the surface of the skin above the regional fat deposit whose reduction is to be accelerated. One acceptable ointment would deliver about $1.2 \times 10^{-9}$ molar forskolin and about $25 \times 10^{-6}$ molar yohimbine as active ingredients to the fat deposit, although other active ingredients and treatment levels would also be acceptable. To deliver this level of active ingredient, higher concentrations in the ointment may be required.

The following examples will serve to illustrate the application of the present invention. Five obese outpatient women who were displeased with their heavy thighs received injections of 0.2 cubic centimeters of a $10^{-5}$ molar sterile saline solution of isoproterenol every four cm around the entire circumference of one thigh each. (Initial studies suggested that the diffusional distance of the active ingredient in such a treatment is about 2 cm. The total amount of injected drug had no observable effect systematically in symptoms, pulse rate, or blood pressure in this initial study on one patient, as the total dosage in this treatment is at a very low level.) The injections were positioned two-thirds of the distance from the greater trochanter to the knee using a one-half inch, 26 gauge needle. The opposite thigh was injected in the same manner using a saline placebo of identical appearance in a blinded fashion. The injections were repeated three times a week for four weeks, and the thigh circumference was measured at the level of the injections at the beginning and at the end of the four-week treatment period. The women were encouraged to exercise by walking and to adhere to a balanced diet restricted to 20 kcal/kg of desirable body weight, or about 1200 calories per day. Four of the five women outpatients lost body weight during the four week treatment period, and all four of these women lost more girth from the thigh treated with isoproterenol injections. The girth changes in the four women who lost weight were 5 cm, 2.5 cm, 1 cm and 1 cm, respectively, where girth change is defined as the decreased girth on the treated thigh minus the decreased girth on the untreated thigh. The fifth women gained ½ pound during the four week treatment period, and had equal amounts of girth change on her thighs bilaterally.

It will now be appreciated that, through the use of this invention, accelerated weight reduction from regional fat desposits may be accomplished during a general weight control program. The selective weight loss from regional fat deposits allows the accelerated reduction of weight and size from those regional fat deposits which ordinarily are reduced more slowly in a weight control program. Consequently, a balanced weight reduction may be achieved, so that normally slowly reducing portions of the body, such as the thighs, may be reduced at a rate comparable with that of the naturally more rapidly reducing portions, such as the abdomen.

Although a particular embodiment of the invention is described in detail for purposes of illustration, various embodiments may be made without departing from the spirit and the scope of the invention. Accordingly, the invention is not to be limited, except as by the appended claims.

I claim:

1. A process for achieving a selective reduction in body weight, comprising the steps of:

delivering specifically to the portion of the body where weight reduction is sought a therapeutically effective amount of an alpha-2 adrenergic inhibitor; and accomplishing a general weight loss program, whereby an acceleration of weight loss is achieved from the portion of the body to which the active ingredient was selectively delivered.

2. The process of claim 1, wherein said delivery step is achieved by injection.

3. The process of claim 1, wherein the active ingredient is specifically delivered to the thighs.

4. The process of claim 1, wherein said delivery step is achieved by topical application to the surface of the skin.

5. The process of claim 1, wherein the alpha-2 adrenergic inhibitor is selected from the group consisting of yohimbine, rauwolscine, piperoxane, phentolamine and dihydroergotamine.

6. A process for accelerated reduction of a regional fat deposit present in a selected portion of the body, comprising the steps of:

introducing specifically into the regional fat deposit a therapeutically effective amount of an alpha-2 adrenergic inhibitor; and undergoing a program of general weight reduction.

7. The process of claim 6, wherein the alpha-2 adrenergic inhibitor is selected from the group consisting of yohimbine, rauwolscine, piperoxane, phentolamine and dihydroergotamine.

8. The process of claim 6, wherein said introducing step is accomplished by injection.

9. The process of claim 6, wherein said introducing step is accomplished by topical application to the surface of the skin.

10. A process for accelerating the reduction of regional fat deposits in a person, comprising the step of:

delivering specifically to the portion of the person's body where weight reduction is sought a therapeutically effective amount of an alpha-2 adrenergic inhibitor.

11. The process of claim 10, wherein the alpha-2 adrenergic inhibitor is selected from the group consisting of yohimbine, rauwolscine, piperoxane, phentolamine, and dihydroergotamine.

12. The process of claim 10, wherein said step of delivering is accomplished by injection.

13. The process of claim 10, wherein said step of delivering is accomplished by topical application to the surface of the skin.

14. The process of claim 10, wherein the portion of the body where weight reduction is sought is the thighs, and the chemical is delivered to the thighs.

* * * * *